(12) United States Patent
Kim (10) Patent No.: US 11,571,250 B2
(45) Date of Patent: Feb. 7, 2023

(54) APPARATUS FOR STABILIZING AIR CIRCULATION AND REMOVING CONTAMINANTS THEREIN DURING MOXIBUSTION THERAPY

(71) Applicant: Young Su Kim, Centreville, VA (US)

(72) Inventor: Young Su Kim, Centreville, VA (US)

( * ) Notice: Subject to any disclaimer, the term of this patent is extended or adjusted under 35 U.S.C. 154(b) by 937 days.

(21) Appl. No.: 16/414,050

(22) Filed: May 16, 2019

(65) Prior Publication Data

US 2020/0360071 A1    Nov. 19, 2020

(51) Int. Cl.
*A61B 18/06* (2006.01)
*B01D 46/00* (2022.01)
*A61H 39/06* (2006.01)
*B01D 46/62* (2022.01)

(52) U.S. Cl.
CPC ............. *A61B 18/06* (2013.01); *A61H 39/06* (2013.01); *B01D 46/0038* (2013.01); *B01D 46/62* (2022.01); *A61B 2018/064* (2013.01); *A61B 2218/008* (2013.01); *A61H 2201/0169* (2013.01); *B01D 2279/00* (2013.01)

(58) Field of Classification Search
CPC .............. A61B 18/06; A61B 2018/064; A61B 2218/008; A61F 2007/0052; A61F 2007/0059; A61F 2007/006; A61F 2007/0069; A61F 7/034; A61H 2201/0153; A61H 2201/0169; A61H 2201/0207; A61H 2201/0221; A61H 2201/1635; A61H 2201/1685; A61H 39/06; B01D 46/0038; B01D 46/62
See application file for complete search history.

(56) References Cited

U.S. PATENT DOCUMENTS

| | | | |
|---|---|---|---|
| 3,946,733 A | 3/1976 | Han | |
| 4,731,050 A | 3/1988 | Harada | |
| 2006/0180160 A1 | 8/2006 | Yang | |
| 2011/0100221 A1* | 5/2011 | Wu | ........................ B01D 46/12 96/64 |

FOREIGN PATENT DOCUMENTS

| | | |
|---|---|---|
| CN | 105769549 A | 7/2016 |
| CN | 109568128 A | 4/2019 |
| KR | 19980064950 A | 10/1998 |

* cited by examiner

*Primary Examiner* — Khadijeh A Vahdat
(74) *Attorney, Agent, or Firm* — Novick, Kim & Lee PLLC; Jae Youn Kim (57) ABSTRACT

The apparatus includes a moxibustion container assembly for localized application of therapeutic herbal smoke originated from gas-producing combustible material, an air pump connectable to the moxibustion container assembly via an inlet tube to supply air to the moxibustion container assembly, a vacuum pump connectable to the moxibustion container assembly via an outlet tube to create a partial vacuum to draw air from the moxibustion container assembly and exhaust air thereafter, and an air purifier connected to the vacuum pump to remove the contaminants in the air exhausted from the vacuum pump.

16 Claims, 10 Drawing Sheets

APPARATUS FOR STABILIZING AIR CIRCULATION AND REMOVING CONTAMINANTS THEREIN DURING MOXIBUSTION THERAPY

TECHNICAL FIELD

The present disclosure relates to an apparatus for moxibustion therapy, and more particularly, to an apparatus for stabilizing air circulation and removing contaminants therein during moxibustion therapy.

RELATED ART

Moxibustion is a form of heat therapy in which dried plant materials called "moxa" are burned on or very near the surface of the skin. Practitioners use moxa to warm regions and meridian points with the intention of stimulating circulation through the points and inducing a smoother flow of blood and qi. Moxa is usually made from the dried leafy material of Chinese mugwort, but it can be made of other substances as well.

During moxibustion, practitioners generally hold a burning moxa stick close to, but not touching, the surface of the skin. In this method, the moxa material is compressed into a stick or pole, looking not unlike an oversized cigar that can be lit and allowed to smolder, producing a unique form of very penetrating heat. Practitioners often do both acupuncture and moxibustion in the same clinic session when appropriate to the diagnosis and treatment strategy. In this combined treatment, the smoldering moxa stick is held over specific areas, often, though not always, corresponding to acupuncture points.

Moxibustion is used for pain due to injury or arthritis, especially in "cold" patterns where the pain naturally feels better with the application of heat, digestive problems and irregular elimination, gynecological and obstetrical conditions, including breech presentation in late term pregnancy, protection against cold and flu strains, etc.

Moxibustion can be classified as traditional moxibustion, drug moxibustion, and modern moxibustion. Traditional moxibustion therapy is the most commonly used in the ancient and contemporary moxibustion clinics, and it is characterized by the use of moxa as burning material and can be divided into direct moxibustion and indirect moxibustion depending on whether moxa is directly in contact with the skin while operating. A moxa cone placed directly on the skin and ignited is called direct moxibustion, while the moxa kept at certain distance from the skin is called indirect moxibustion. The insulating materials of indirect moxibustion can be air, garlic, ginger, aconite, salt, and so forth. Drug moxibustion, also named nature moxibustion, uses irritant drugs (such as cantharis, garlic, and semen sinapis) to coat the surface of acupoints and make local skin flushed and blistered to cure diseases. Modern moxibustions, such as microwave moxibustion, laser moxibustion, and electrothermal moxibustion, are used to simulate traditional moxibustion stimulation factors by physical or chemical methods to achieve therapeutic effects of moxibustion.

For purposes of topical application of moxibustion products there has been employed a chambered apparatus having a grating spaced from the skin upon which the herbal leaves are burned, the combustion products passing across the skin and freely out of the apparatus through a series of openings formed by a series of arches at the locus of engagement of the apparatus. In order to reduce the number of treatments and the period duration of treatments, U.S. Pat. No. 3,946,733 suggests an improved moxibustion apparatus for treatment of a user by periodic localized topical applications of therapeutic combustion gases, including an open-mouthed combustion chamber adapted to define with the user's skin a topical treatment zone, a means for generating therapeutic combustion gases within the chamber, and a means for pressurizing the gases within the topical treatment zone during treatment periods.

However, it is difficult for a practitioner to carry this chamber shaped apparatus by hand and periodically apply moxibustion treatments at various regions. In addition, although an external air pump may provide pressurized air into the chamber, there has not been employed a system for drawing gas or smoke generated during therapy and effectively removing contaminants in the air while continuously supplying pressured air into the chamber so as to provide clean and pleasant therapeutic environment to patients.

Thus, there is a need for new apparatus for stabilizing air circulation and removing contaminants therein during moxibustion therapy that overcome the above-identified problems.

SUMMARY

The present disclosure provides an apparatus for stabilizing air circulation and removing contaminants during moxibustion therapy.

According to one embodiment of the present disclosure, the apparatus may comprise a moxibustion container assembly for localized application of therapeutic herbal smoke originated from gas-producing combustible material, an air pump connectable to the moxibustion container assembly via an inlet tube to supply air to the moxibustion container assembly, a vacuum pump connectable to the moxibustion container assembly via an outlet tube to create a partial vacuum to draw air from the moxibustion container assembly and exhaust air thereafter, and an air purifier connected to the vacuum pump to remove the contaminants in the air exhausted from the vacuum pump.

A silencer may be disposed between the vacuum pump and the air purifier so as to reduce sound pressure of the air exhausted from the vacuum pump.

The apparatus may further comprise a ventilation duct connected to the vacuum pump so as to guide air from an outside atmosphere into the vacuum pump, wherein an intake duct is fixed to an inlet of the ventilation duct.

The moxibustion container assembly may be configured to be detachably connected to the apparatus so as to be replaced according to various therapeutic applications.

The moxibustion container assembly may comprise a container for carrying the gas-producing combustible material, the container having an opening at a bottom surface thereof, a grip handle fixed to an external surface of the container, and a lid configured to cover a top portion of the container.

The container of the moxibustion container assembly may comprise an inner chamber configured to support the gas-producing combustible material, the inner chamber including a bottom plate having a plurality of holes, an outer chamber enclosing the inner chamber and defining an annular plenum therewith, and a bottom chamber disposed under the inner chamber so as to communicate therewith through the plurality of holes, the bottom chamber having the opening at a bottom surface thereof.

The container of the moxibustion container assembly may further comprise an inner lid configured to cover a top portion of the inner chamber.

The outer chamber may have an inlet hole connected to the inlet tube so as to supply air into the annular plenum from the air pump, and the bottom chamber may have an outlet hole connected to the outlet tube so as to draw air from the bottom chamber into the vacuum pump.

The bottom chamber may have a balancing hole for communicating with an outside atmosphere, and the balancing hole may be configured to be closed or opened according to an operation of the apparatus.

At least a portion of the top lid may be formed by an elastic material.

The purifier may comprise a body, an air-intake disposed at a bottom of the body, one or more filters stacked on or above the air-intake within the body, a fan configured to generate an air stream between the one or more filters within the body, and an outlet diffuser disposed on an outer surface of the body so as to deliver the filtered air stream to an outside atmosphere.

The moxibustion container assembly may further include an inlet guide tube connected to the container and disposed inside the grip handle, and the inlet guide tube configured to supply air to the container.

According to another embodiment of the present disclosure, an apparatus may comprise a first and a second moxibustion container assemblies for localized application of therapeutic herbal smoke originated from gas-producing combustible material, a first and a second air pumps respectively connectable to the first and the second moxibustion container assemblies via a first and a second inlet tubes, respectively, so as to supply air to the first and the second moxibustion container assemblies, a first and a second vacuum pumps respectively connectable to the first and the second moxibustion container assemblies via a first and a second outlet tubes, respectively, so as to create a partial vacuum to draw air from the first and the second moxibustion container assemblies and exhaust air thereafter, and an air purifier connected to the first and second vacuum pumps to remove contaminants in the air exhausted from the first and second vacuum pumps.

The apparatus may further comprise a first and a second silencers, the first and the second silencers respectively being disposed between the first vacuum pump and the air purifier and between the second vacuum pump and the air purifier, so as to reduce sound pressure of the air exhausted from the first and the second vacuum pumps.

The apparatus also may further comprise a ventilation duct connected to the first and the second vacuum pumps so as to guide air from an outside atmosphere into the first and the second vacuum pumps, wherein an intake duct is fixed to an inlet of the ventilation duct.

The apparatus may be controlled such that, when the first moxibustion container assembly is used, the second vacuum pump is on, the first vacuum pump is off, the first air pump is on, and the air purifier is on, so that air is supplied to the first moxibustion container assembly from the first air pump and air is drawn from the first moxibustion container assembly by a pulling force generated by a fan in the purifier and a pressure applied into the first moxibustion container assembly by the supplied air from the first air pump.

The apparatus may be controlled such that, when the first moxibustion container assembly is used, the first vacuum pump is on, the balancing hole of the first moxibustion container assembly is open, the first air pump is on, and the air purifier is on, so that air is supplied to the first moxibustion container assembly from the first air pump and air is drawn from the first moxibustion container assembly by a suction force generated by the vacuum pump while air pressure inside the first moxibustion container assembly is reduced by air communication between the first moxibustion container assembly and an outside atmosphere through the balancing hole.

The apparatus may also be controlled such that, when the first moxibustion container assembly is used, both the first and second vacuum pumps are off, the first air pump is on, and the air purifier is on, so that air is supplied to the first moxibustion container assembly from the first air pump and air is drawn from the first moxibustion container assembly by a pulling force generated by the fan in the purifier and a pressure applied into the first moxibustion container assembly by the supplied air from the first air pump.

According to another embodiment of the present disclosure, an apparatus may comprise a moxibustion container assembly for localized application of therapeutic herbal smoke originated from gas-producing combustible material. In this embodiment, the moxibustion container assembly includes a container for carrying the gas-producing combustible material, the container having an opening at a bottom surface thereof, a grip handle fixed to an external surface of the container, and an inlet guide tube connected to the container and disposed inside the grip handle, the inlet guide tube being configured to supply air to the container.

BRIEF DESCRIPTION OF THE DRAWINGS

The teachings of the present invention can be more readily understood by considering the following detailed description in conjunction with the accompanying drawings.

DETAILED DESCRIPTION

Reference will now be made in detail to embodiments of the present disclosure, examples of which are illustrated in the accompanying drawings. It is noted that wherever practicable, similar or like reference numbers may be used in the drawings and may indicate similar or like elements.

The drawings depict embodiments of the present disclosure for purposes of illustration only. One skilled in the art would readily recognize from the following description that alternative embodiments exist without departing from the general principles of the present disclosure.

Figure 1:
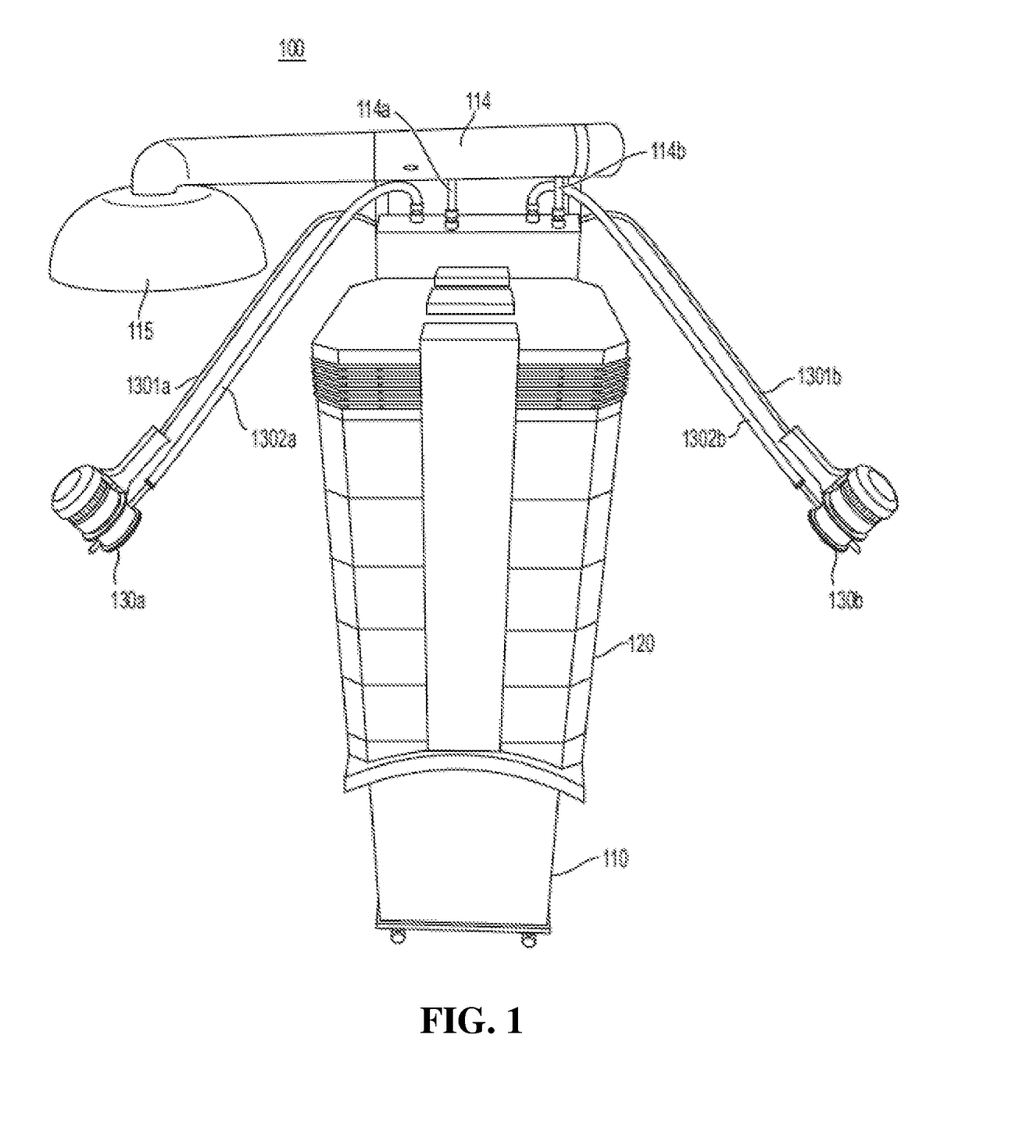
FIG. 1 is a perspective view showing a front side of the apparatus according to one embodiment of the present invention.
Figure 2:
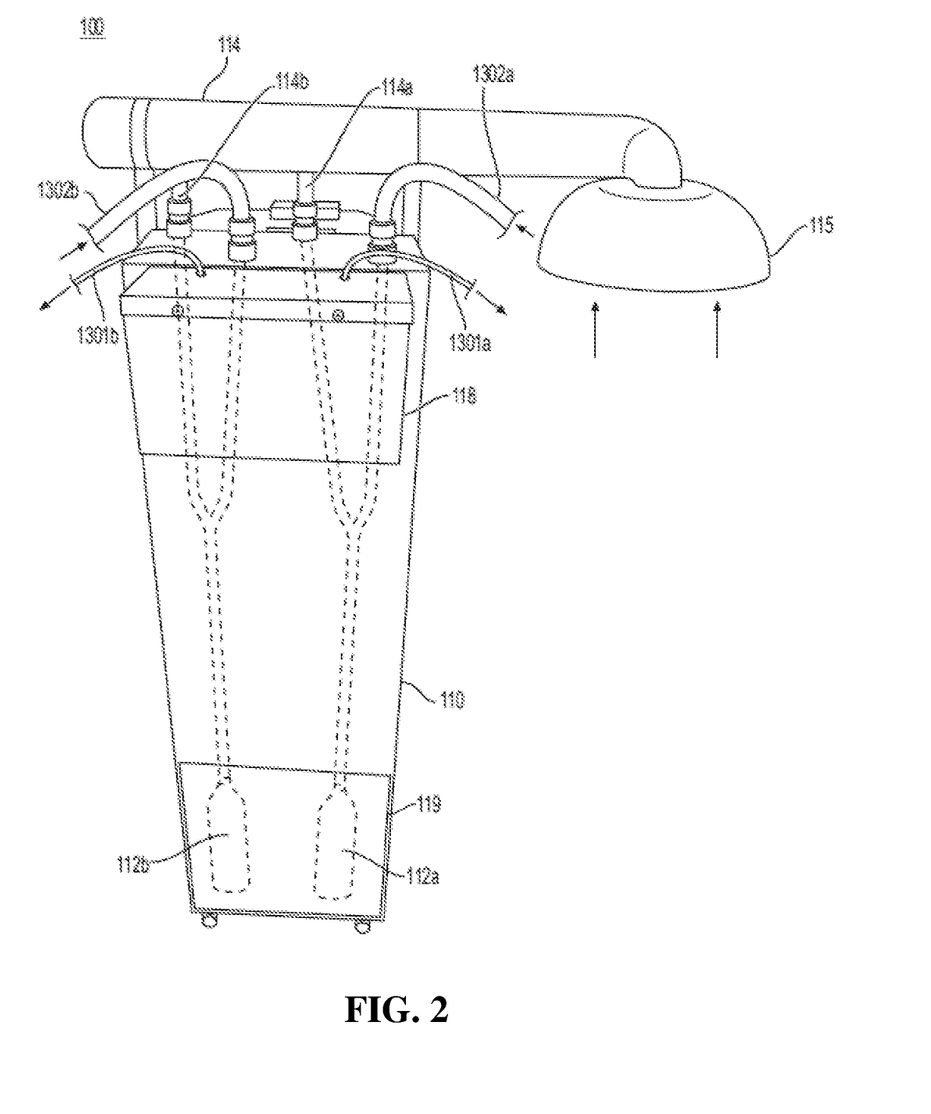
FIG. 2 is a perspective view showing a back side of the apparatus according to one embodiment of the present invention.

FIGS. 1 and 2 are perspective views respectively showing a front side and a back side of the apparatus according to one embodiment of the present invention.

As shown in FIGS. 1 and 2, the apparatus 100 may include a main body 110 and a purifier 120 mounted on the main body 110. A first pair of inlet and outlet tubes 1301a and 1302a can be extended from the main body 110 and connected to a first handheld moxibustion device, i.e., is a first handheld moxibustion container assembly, 130a, and a second pair of inlet and outlet tubes 1301b and 1302b can be extended from the main body 110 and connected to a second hand-held moxibustion device, i.e., a second handheld moxibustion container assembly, 130b. A first and a second air pumps 111a and 111b and a first and a second vacuum devices 112a and 112b are disposed within the main body 110 (see FIGS. 3 and 4). The first and the second inlet tubes 1301a and 1301b are respectively connected to the first and the second air pumps 111a and 111b and the first and the second outlet tubes 1302a and 1302b are respectively connected to the first and the second vacuum devices 112a and 112b (see FIG. 2). In this embodiment, the first and the second air pumps 111a and 111b may be accommodated within a projected casing 118 of the main body 110 although not illustrated in FIG. 2, and the first and the second vacuum devices 112a and 112b may be accommodated in a lower part of the main body as illustrated in FIG. 2. An opening for maintenance access can be formed near the first and the second vacuum devices 112a and 112b, and an access panel 119 can be attached to block the opening in normal operation of the apparatus 100. A ventilation duct 114 is mounted on top of the main body 110, and a first and a second suction tubes 114a and 114b from the first and the second vacuum devices 112a and 112b are connected to the ventilation duct 114 so as to guide air from the outside atmosphere into the vacuum devices 112a and 112b. Herein, an intake duct 115 is fixed to an inlet of the ventilation duct 114.

Figure 3:
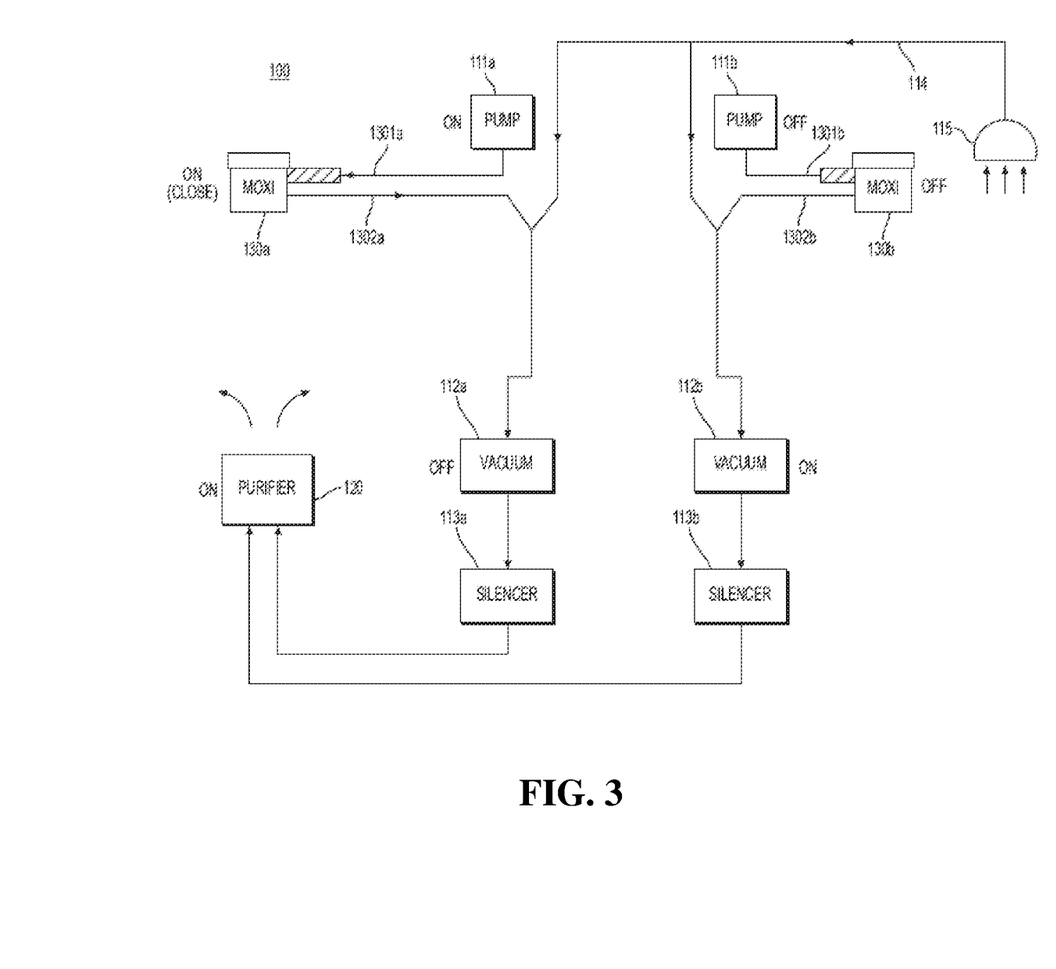
FIG. 3 is a schematic view showing a first controlled system of stabilizing air circulation and removing contaminants during moxibustion therapy using the apparatus according to one embodiment of the present invention.
Figure 4:
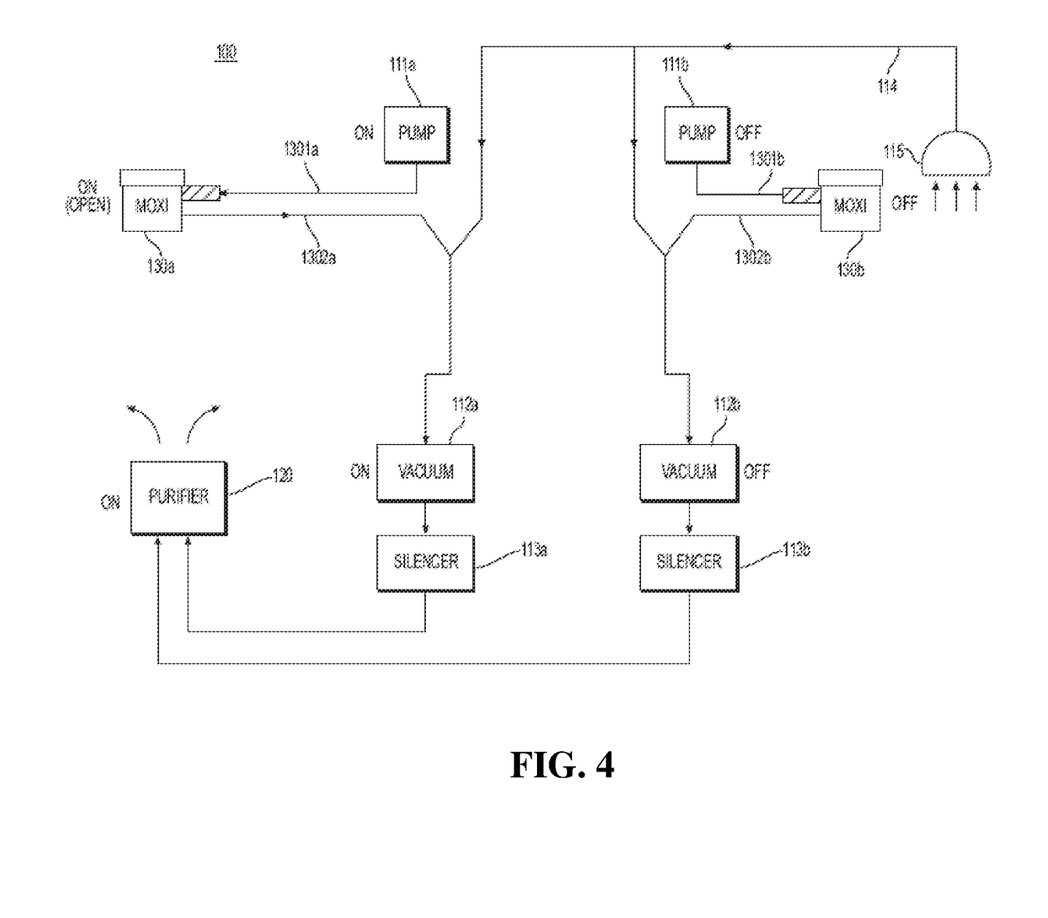
FIG. 4 is a schematic view showing a second controlled system of stabilizing air circulation and removing contaminants during moxibustion therapy using the apparatus according to one embodiment of the present invention.

FIGS. 3 and 4 are schematic views showing a controllable system for stabilizing air circulation and removing contaminants during moxibustion therapy using the apparatus according to one embodiment of the present invention.

With reference to FIGS. 3 and 4, the apparatus 100 includes the first and the second hand-held moxibustion devices 130a and 130b, the first and the second air pumps 111a and 111b respectively connectable to the first and the second moxibustion devices 130a and 130b via the first and a second inlet tubes 1301a and 1301b, the first and the second vacuum devices 112a and 112b respectively connectable to the first and the second moxibustion devices 130a and 130b via the first and the second outlet tubes 1302a and 1302b, and the air purifier 120 connected to the first and second vacuum devices 112a and 112b to remove contaminants in the air exhausted from the first and second vacuum devices 112a and 112b. In this embodiment, each of the first and the second inlet tubes 1301a and 1301b may be a flexible plastic tube, which is connected to an inlet of each moxibustion device (130a or 130b) by each inlet fitting. Also, each of the first and the second outlet tubes 1302a and 1302b may be a flexible metal tube, which is connected to an outlet of each moxibustion device (130a or 130b) by each outlet fitting.

Further, a first and a second silencers 113a and 113b can be respectively disposed between the first vacuum device 112a and the air purifier 120 and between the second vacuum device 112b and the air purifier 120.

The first and the second air pumps 111a and 111b are configured to supply air to the first and the second moxibustion devices 130a and 130b, respectively. In this embodiment, these air pumps may be electric type air pumps each providing constant and uniform air flow by electric power.

The first and the second vacuum devices 112a and 112b are configured to create a partial vacuum to draw air via inlets from the first and the second moxibustion devices 130a and 130b, respectively, and exhaust air thereafter through outlets, which are connected to the first and the second silencer 113a and 113b via metal tubes. In this embodiment, each vacuum device (112a or 112b) may be a motor driven vacuum pump or a suction pump which is equivalent of the vacuum pump, but not limited thereto. The inlet and the outlet of each vacuum device (112a or 112b) may be aligned in a same axis. Each vacuum device (112a or 112b) may include a filter therein, and accordingly, in this embodiment, the drawn air from each moxibustion device (130a or 130b) may be partially filtered before being exhausted.

The first and the second silencers 113a and 113b are configured to reduce sound pressure of the air exhausted from the first and the second vacuum devices 112a and 112b. In this embodiment, each silencer (113a or 113b) may be a muffler engineered as an acoustic device to reduce the loudness of the sound pressure, through which the exhaust air from the vacuum device (112a or 112b) at high velocity is abated by a series of passages and chambers lined with roving fiberglass insulation and/or resonating chambers harmonically tuned to cause destructive interference, wherein opposite sound waves cancel each other out.

As also shown in FIGS. 1 and 2, the ventilation duct 114 communicates with the first and second vacuum devices 112a and 112b via the suction tubes 114a and 114b, and the intake duct 115 is fixed to the inlet of the ventilation duct 114.

Each of the hand-held moxibustion devices 130a and 130b is configured to be used for localized application of therapeutic herbal smoke originated from gas-producing combustible herbal material such as a dried moxa to the body of the patient for treatment of bodily ills, and configured to be detachably connected to the apparatus 100 so as to be replaced according to various therapeutic applications.

Figure 5:
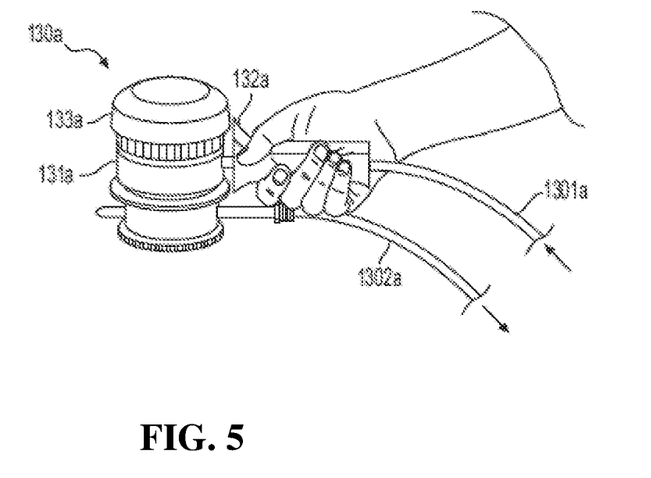
FIG. 5 is a perspective view of a hand-held moxibustion container assembly of the apparatus according to one embodiment of the present invention.
Figure 6:
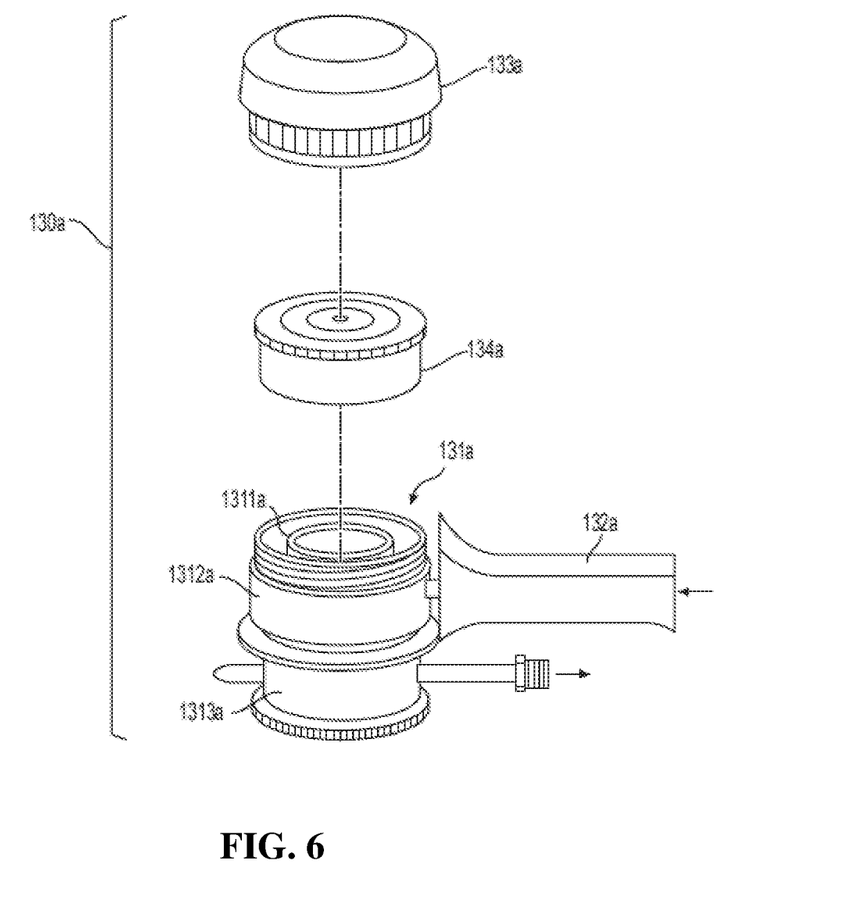
FIG. 6 is an exploded view of the hand-held moxibustion container assembly of the apparatus according to one embodiment of the present invention.
Figure 7:
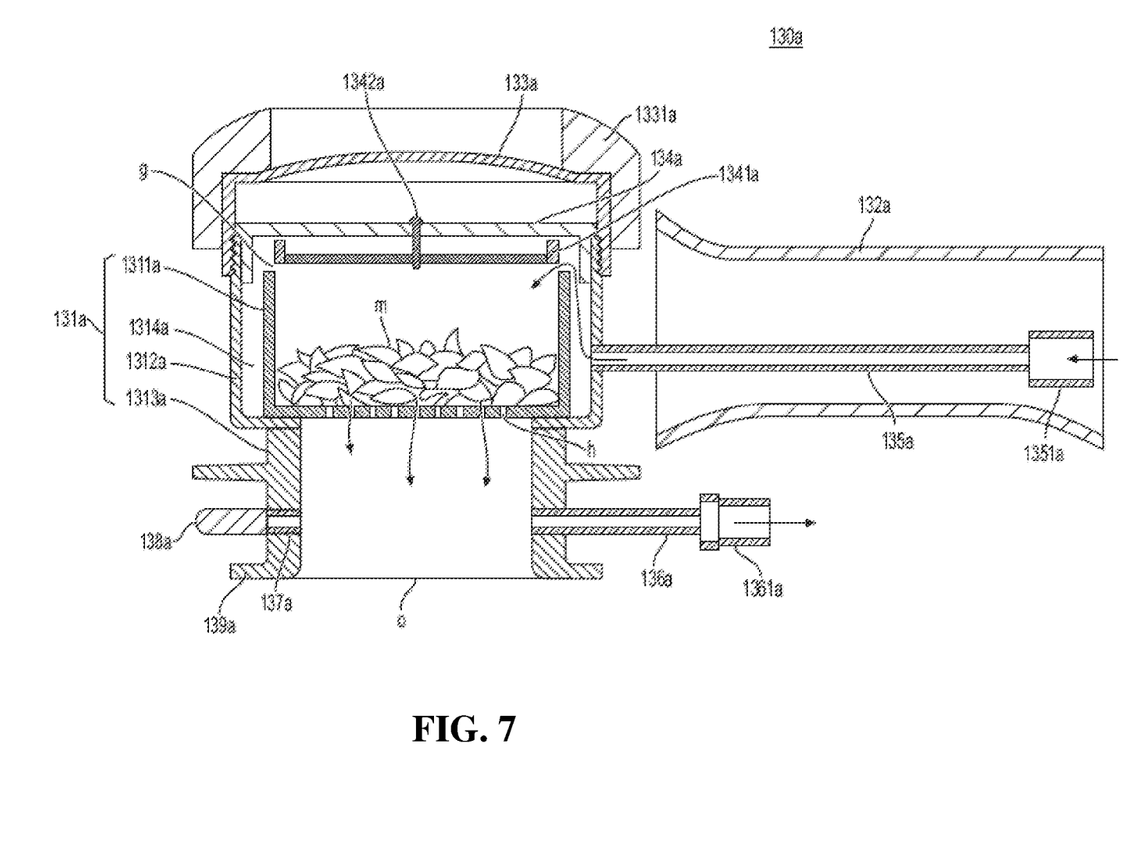
FIG. 7 is a cross-sectional view of the hand-held moxibustion container assembly of the apparatus according to one embodiment of the present invention.

FIGS. 5 to 7 shows a detailed structure of each hand-held moxibustion device, a container assembly, 130a, 130b of the apparatus according to one embodiment of the present invention. Since the first hand-held moxibustion device 130a has the same structure as the second hand-held moxibustion device 130b, only the first hand-held device 130a is shown in detail in FIGS. 5-7 and described accordingly as set forth below.

As shown in FIGS. 5 to 7, the first hand-held moxibustion device 130a includes a container 131a for carrying and containing the gas-producing combustible material, a grip handle 132a fixed to an external surface of the container 131a, and a top lid 133a configured to cover a top portion of the container 131a. The container 131a has an opening (o) at its bottom surface to define a topical treatment zone on the patient's skin. The grip handle 132a accommodates an inlet guide tube 135a (see FIG. 7), which is configured to be detachably connected to the inlet tube 1301a through an inlet fitting 1351a.

The container 131a includes an inner chamber 1311a adapted to support the gas-producing combustible material, an outer chamber 1312a enclosing the inner chamber 1311a and defining an annular plenum 1314a therewith, and a bottom chamber 1313a disposed under the inner chamber 1311a so as to communicate therewith through the plurality of holes. The container 131a further includes an inner lid 134a configured to cover a top portion of the inner chamber 1311a. However, as shown in FIG. 7, the inner lid 134a does not seal the inner chamber 1311a, because an inner diameter of the inner lid 134a is larger than a diameter of the inner chamber 1311a to form a radial gap (g) between them. Through this radial gap (g), the interior of the inner chamber 1311a is communicated with the annular plenum 1314a. On an upper portion of an outer surface of the outer chamber 1312a, a thread is formed to be engaged with the top lid 133a, an internal surface of which has a corresponding thread. At least a portion of the top lid 133a is formed by an elastic material 1331a to prevent it from being broken when it is fallen during the moxibustion treatment.

The inner chamber 1311a includes a bottom plate having the plurality of holes (h), on which a quantity of moxa (e.g., herbal leaves) (m) is supported. The inner chamber 1311a is made of metal to endure high temperature heat generated from burning moxa. A metal plate 1341a can be also mounted inside the inner lid 133a to cover the inner chamber 1311a with the radial gap (g) mentioned above. The height of the metal plate 1341a may be adjusted by a screw 1342a at the center of the metal plate 1341a with respect to the inner lid 134a to adjust a size of the radial gap (g) between the inner lid 134a and the inner chamber 1311a.

The outer chamber 1312a has an inlet hole connected to the inlet guide tube 135a so as to supply air into the annular plenum 1314a from the air pump. The outer chamber 1312a may be made of plastic material to reduce the weight of the container, but not limited thereto.

The bottom chamber 1313a has an outlet hole connected to the outlet guide tube 136a, which is configured to be connected to the outlet tube 1302a through an outlet fitting 1361a, so as to draw air from the bottom chamber 1313a into the vacuum device 112a, and has the opening (o) at a bottom surface thereof. The bottom chamber 1313a also has an balancing hole 137a for communicating with the outside atmosphere, and the balancing hole 137a is configured to be closed or open according to an operation of the apparatus 100. In this embodiment, a threaded plug 138a may be used to close or open the balancing hole 137a, as shown in FIG. 7. The bottom chamber 1313a may further include a radially extended bottom plate 139a, a bottom surface of which may form a radial lip around the opening (o) to be directly contacted with the skin of the patient.

In operation, when the air pump 111a is on, a quantity of air, determined by the air pump, is constantly delivered into the plenum 1314a, and the air passes uniformly through the radial gap (g) between the inner lid 134a (more particularly, metal plate 1341a) and the inner chamber 1311a into the interior of the inner chamber 1311a, thereby accelerating combustion of the moxa (m). Then, overly generated smoke or gas enclosed in the bottom chamber 1313a may be drawn into the outlet tube 1302a by the operation of the vacuum device 112a and/or the purifier 120.

Figure 8:
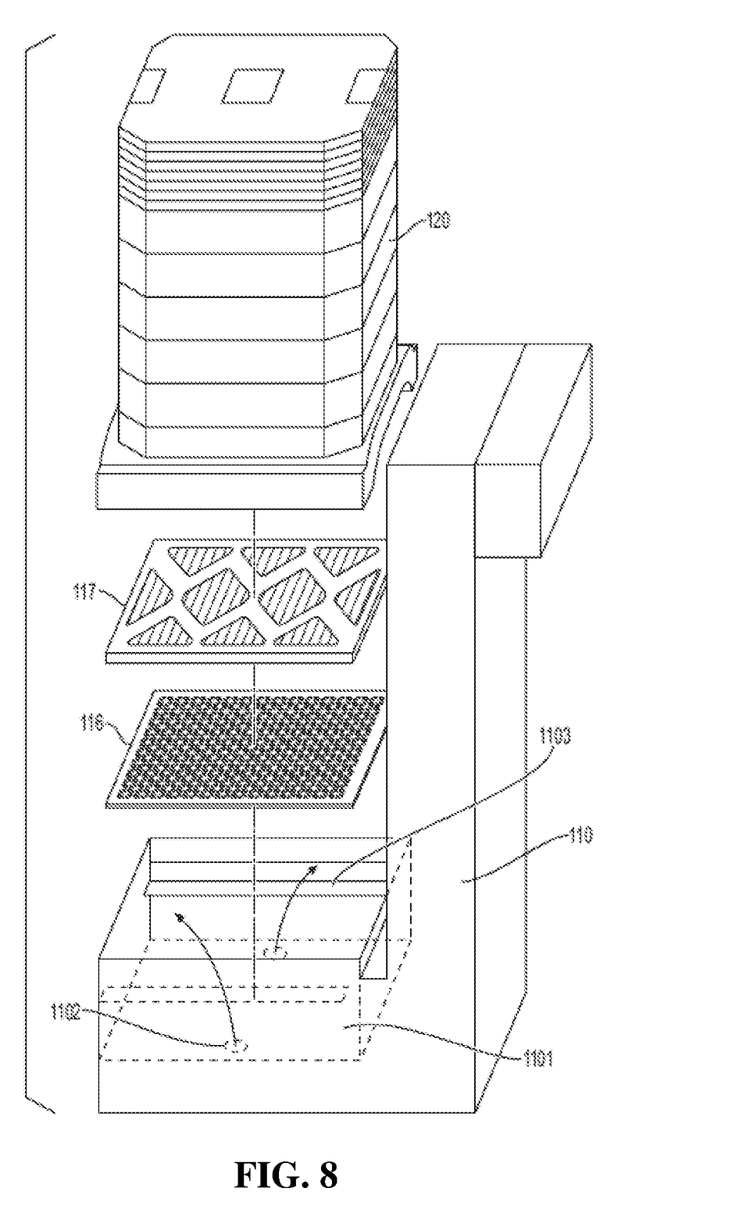
FIG. 8 is an exploded view showing an assembly relationship of a purifier with a main body of the apparatus according to one embodiment of the present invention.
Figure 9:
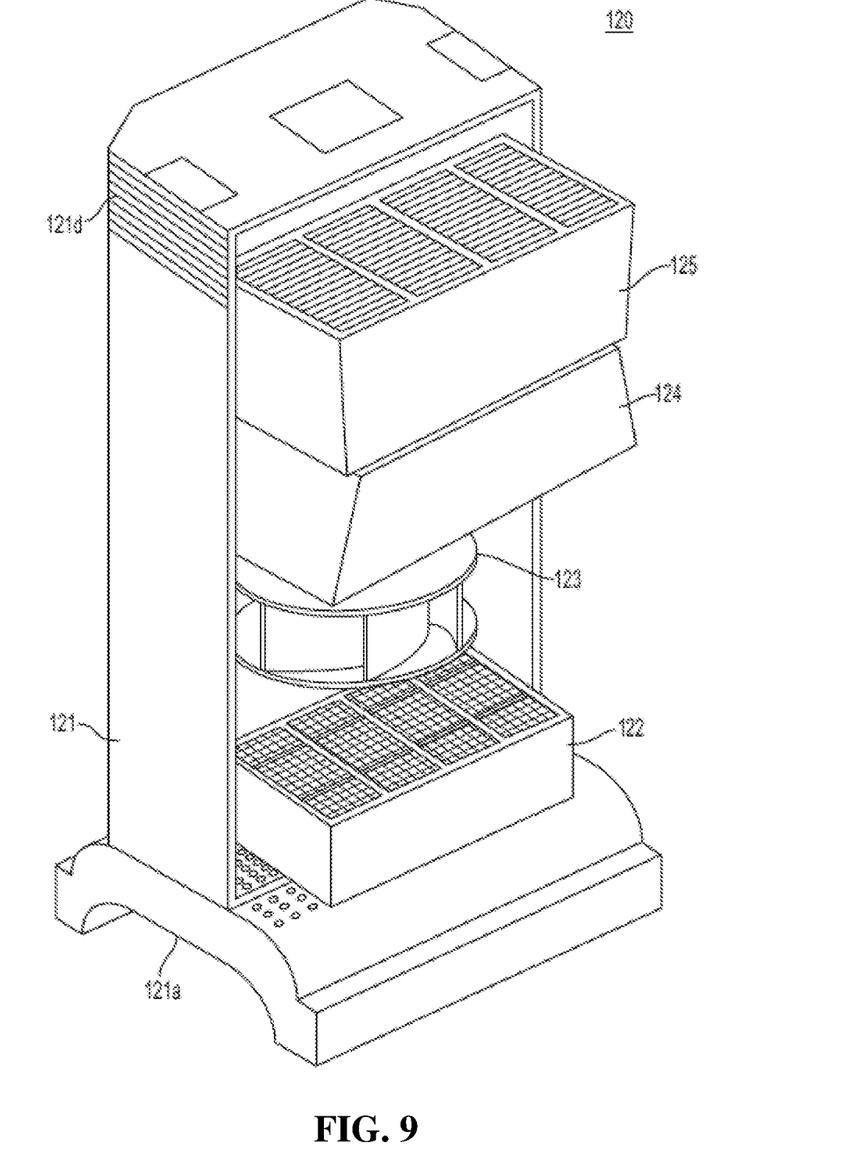
FIG. 9 is a perspective view of the purifier of the apparatus according to one embodiment of the present invention.
Figure 10:
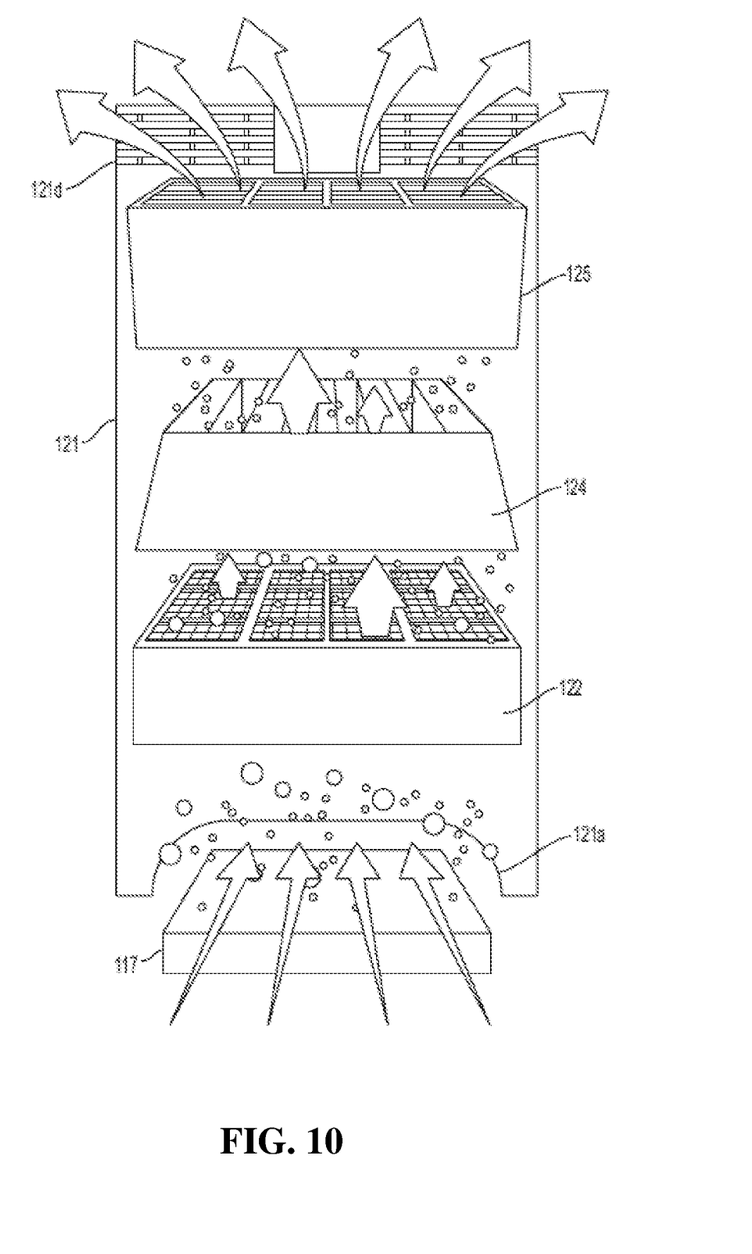
FIG. 10 is a schematic view showing an air stream purified through a filtering system in the apparatus according to one embodiment of the present invention.

FIG. 8 is an exploded view showing the assembly relationship of the purifier with the main body of the apparatus, FIG. 9 is a perspective view of the purifier of the apparatus, and FIG. 10 is a schematic view showing air stream purified through a filtering system in the apparatus according to one embodiment of the present invention.

As shown in FIG. 8, the purifier 120 is mounted on a base cabinet 1101 of the main body 110. On the bottom surface of the base cabinet 1101, a pair of outlet holes 1102 for communicating with a pair of metal tubes extended from the pair of silencers 113a and 113b are formed (see FIGS. 3 and 4). A grating plate 116 is disposed on an extended frame 1103 from the inner surface of the base cabinet 1101, and a supplemental filter 117 may be disposed on the grating plate 116. On the supplemental filter 117, the purifier 120 is mounted to allow the entrance of the air stream exhausted from the pair of outlet holes 1102 on the bottom surface of the base cabinet 1101, through the supplemental filter 117.

As shown in FIG. 9, the purifier 120 includes a body 121, an air-intake 121a disposed at the bottom of the body 121, three different types of filters 122, 124 and 125 stacked on or above the air-intake portion 121a within the body 121, a fan 123 configured to generate air stream between the three filters 122, 124 and 125 within the body 121, and an outlet diffuser 121d formed on an outer surface of the body 121 so as to deliver the filtered air stream to the outside atmosphere. In this embodiment, the fan 123 may be a centrifugal type of fan to reduce the noise. The three filters may comprise a pre-filter 122, which eliminates micro-particles, a gas and odor filter 124, which protects against chemicals, odors and gases in the air stream with dual-media filtration, and a HEPA (High Efficiency Particulate Air) filter 125, which protects against particles of all sizes, including ultrafine particles.

As shown in FIG. 10, the air from the pair of silencers 113a and 113b are entered into the purifier 120 through the air-intake 121a after preliminarily filtered in the supplemental filter 117, and then flows through the three different filters 122, 124 and 125 on the air stream generated by the pan 123. During these multiple filtrations, all contaminants including particles, gases and odors are effectively removed, and only clean air is exhausted through the outlet diffuser 121d formed on an outer surface of the body 121 into the outside atmosphere in multiple directions, thereby reducing noise and preventing drafts.

With reference to FIGS. 3 and 4 again, the various controlled systems or methods for stabilizing air circulation and removing contaminants during moxibustion therapy using the apparatus will be explained as set forth below.

In the first controlled system, as illustrated in FIG. 3, the apparatus 100 can be controlled such that, when the first moxibustion device 130a is used (while the balancing hole 137a of the first moxibustion device 130a is closed), the second vacuum device 112b can be on, the first vacuum device 112a can be off, the first air pump 111a can be on, and the air purifier 120 can be on. When using the first moxibustion device 130a, the first vacuum device 112a should be turned off, because the suction force from the first vacuum device 112a may significantly reduce heat transfer from the moxibustion device onto the skin and may even overly suck up the skin during the treatment. In this system, air is constantly supplied to the first moxibustion device 130a from the first air pump 111a. However, since the first vacuum device 112a is off, air can be drawn from the first moxibustion device 130a mostly by a pulling force generated by the fan 123 in the purifier 120 and a pressure applied into the first moxibustion device 130a by the supplied air from the first air pump 111a. Meanwhile, since the second vacuum device 112b is on, while the second air pump 111b is off, air can be forcibly drawn from the outside atmosphere through the intake duct 115 by a suction force generated by the second vacuum device 112b. Then, the air passed through the first vacuum device 112a, which is currently off, can be entered into the purifier 120 after its sound pressure is reduced in the first silencer 113a, and then delivered out into the outside atmosphere as clean air after the multiple filtrations. Also, the air forcibly exhausted from the second vacuum device 112b, which is currently on, can be entered into the purifier 120 after its sound pressure is also reduced in the second silencer 113b, and then delivered out into the outside atmosphere as clean air after the multiple filtrations, along with the air from the first silencer 113a.

In an alternative control, the second vacuum device 112b may also be turned off while others are the same with the first controlled system to further reduce noise mostly occurred at the second vacuum device 112b. In this alternative control, air is constantly supplied to the first moxibustion device 130a from the first air pump 111a. However, since both the first and the second vacuum devices 112a and 112b are off, air is drawn from the first moxibustion device 130a only by a pulling force generated by the fan 123 in the purifier 120 and a pressure applied into the first moxibustion device 130a by the supplied air from the first air pump 111a.

In the second controlled system, as illustrated in FIG. 4, the apparatus 100 can be controlled such that, when the first moxibustion device 130a is used, the first vacuum device 112a can be on, the balancing hole 137a (see FIG. 7) of the first moxibustion device 130a can be open, the first air pump 111a can be on, and the air purifier 120 can be on. Although the first vacuum device 130a is turned on in contrast to the first controlled system, the suction force from the first vacuum device 112a may neither significantly reduce heat transfer from the moxibustion device onto the skin nor overly suck up the skin during the treatment, because the balancing hole 137a is open. In this system, air is constantly supplied to the first moxibustion device 130a from the first air pump 111a. Since the first vacuum device 112a is on, air can be drawn from the first moxibustion device 130a mostly by a suction force generated by the first vacuum device 112a while air pressure inside the first moxibustion device 130a is reduced by air communication between the first moxibustion device 130a and the outside atmosphere through the balancing hole 137a. Also, air can be forcibly drawn from the outside atmosphere through the intake duct 115 by a suction force generated by the first vacuum device 112a. Then, the air forcibly exhausted from the first vacuum device 112a, which is currently on, can be entered into the purifier 120 after its sound pressure is reduced in the first silencer 113a, and then delivered out into the outside atmosphere as clean air after the multiple filtrations. Also, the air passed through the second vacuum device 112b, which is currently off, can be entered into the purifier 120 after its sound pressure is also reduced in the second silencer 113b, and then delivered out into the outside atmosphere as clean air after the multiple filtrations, along with the air exhausted from the first vacuum device 112a.

Embodiments of the present disclosure have been described in detail. Other embodiments will become apparent to those skilled in the art from consideration and practice of the present disclosure. Accordingly, it is intended that the specification and the drawings be considered as exemplary and explanatory only, with the true scope of the present disclosure being set forth in the following claims.

What is claimed is:

1. An apparatus for stabilizing air circulation and removing contaminants therein during moxibustion therapy, the apparatus comprising:
    a main body;
    a moxibustion container assembly for localized application of therapeutic herbal smoke originated from gas-producing combustible material;
    an inlet tube extended from the main body and detachably connected to the moxibustion container assembly;
    an outlet tube extended from the main body and detachably connected to the moxibustion container assembly;
    an air pump, which is disposed within the main body and which is connectable to the moxibustion container assembly via the inlet tube to supply air to the moxibustion container assembly;
    a vacuum or suction pump, which is disposed within the main body and which is connectable to the moxibustion container assembly via the outlet tube to create a partial vacuum to draw air from the moxibustion container assembly and exhaust air thereafter; and
    an air purifier connected to the vacuum or suction pump to remove the contaminants in the air exhausted from the vacuum or suction pump.

2. The apparatus of claim 1, further comprising a silencer disposed between the vacuum or suction pump and the air purifier so as to reduce sound pressure of the air exhausted from the vacuum or suction pump.

3. The apparatus of claim 1, further comprising a ventilation duct connected to the vacuum or suction pump so as to guide air from an outside atmosphere into the vacuum or suction pump, wherein an intake duct is fixed to an inlet of the ventilation duct.

4. The apparatus of claim 1, wherein the moxibustion container assembly is configured to be detachably connected to the main body of the apparatus so as to be replaced according to various therapeutic applications.

5. The apparatus of claim 4, wherein the moxibustion container assembly comprises:
    a container for carrying the gas-producing combustible material, the container having an opening at a bottom surface thereof;
    a grip handle fixed to an external surface of the container; and
    a lid configured to cover a top portion of the container.

6. The apparatus of claim 5, wherein the container of the moxibustion container assembly comprises:
    an inner chamber configured to support the gas-producing combustible material, the inner chamber including a bottom plate having a plurality of holes;
    an outer chamber enclosing the inner chamber and defining an annular plenum therewith; and
    a bottom chamber disposed under the inner chamber so as to communicate therewith through the plurality of holes, the bottom chamber having the opening at a bottom surface thereof.

7. The apparatus of claim 6, wherein the container of the moxibustion container assembly further comprising an inner lid configured to cover a top portion of the inner chamber.

8. The apparatus of claim 6, wherein the outer chamber has an inlet hole connected to the inlet tube so as to supply air into the annular plenum from the air pump,
    wherein the bottom chamber has an outlet hole connected to the outlet tube so as to draw air from the bottom chamber into the vacuum or suction pump.

9. The apparatus of claim 8, wherein the bottom chamber has a balancing hole for communicating with an outside atmosphere, and the balancing hole is configured to be closed or opened according to an operation of the apparatus.

10. The apparatus of claim 5, wherein at least a portion of the top lid is formed by an elastic material.

11. The apparatus of claim 5, wherein the moxibustion container assembly further includes an inlet guide tube connected to the container and disposed inside the grip handle, the inlet guide tube being configured to be detachably connected to the inlet tube and being configured to supply air to the container.

12. The apparatus of claim 1, wherein the purifier comprises:
a body;
an air-intake disposed at a bottom of the body;
one or more filters stacked on or above the air-intake within the body;
a fan configured to generate an air stream between the one or more filters within the body; and
an outlet diffuser disposed on an outer surface of the body so as to deliver the filtered air stream to an outside atmosphere.

13. An apparatus for stabilizing air circulation and removing contaminants during moxibustion therapy, the apparatus comprising:
a main body;
a first and a second moxibustion container assemblies for localized application of therapeutic herbal smoke originated from gas-producing combustible material;
a first inlet tube extended from the main body and detachably connected to the first moxibustion container assembly and a second inlet tube extended from the main body and detachably connected to the second moxibustion container assembly;
a first outlet tube extended from the main body and detachably connected to the first moxibustion container assembly and a second outlet tube extended from the main body and detachably connected to the second moxibustion container assembly;
a first and a second air pumps respectively connectable to the first and the second moxibustion container assemblies via the first and the second inlet tubes, respectively, so as to supply air to the first and the second moxibustion container assemblies, wherein the first and second air pumps are disposed within the main body;
a first and a second vacuum or suction pumps respectively connectable to the first and the second moxibustion container assemblies via the first and the second outlet tubes, respectively, so as to create a partial vacuum to draw air from the first and the second moxibustion container assemblies and exhaust air thereafter, wherein the first and a second vacuum or suction pumps are disposed within the main body; and
an air purifier connected to the first and second vacuum or suction pumps to remove contaminants in the air exhausted from the first and second vacuum or suction pumps.

14. The apparatus of claim 13, further comprising a first and a second silencers, the first and the second silencers respectively being disposed between the first vacuum or suction pump and the air purifier and between the second vacuum or suction pump and the air purifier, so as to reduce sound pressure of the air exhausted from the first and the second vacuum or suction pumps.

15. The apparatus of claim 13, further comprising a ventilation duct connected to the first and the second vacuum or suction pumps so as to guide air from an outside atmosphere into the first and the second vacuum or suction pumps, wherein an intake duct is fixed to an inlet of the ventilation duct.

16. An apparatus for stabilizing air circulation and removing contaminants therein during moxibustion therapy, the apparatus comprising:
a main body;
a moxibustion container assembly for localized application of therapeutic herbal smoke originated from gas-producing combustible material,
an inlet tube extended from the main body and detachably connected to the moxibustion container assembly;
an outlet tube extended from the main body and detachably connected to the moxibustion container assembly;
an air-pump, which is disposed within the main body and which is connectable to the moxibustion container assembly via the inlet tube to supply air to the moxibustion container assembly;
a vacuum or suction pump, which is disposed within the main body and which is connectable to the moxibustion container assembly via the outlet tube to create a partial vacuum to draw air from the moxibustion container assembly and exhaust air thereafter;
wherein the moxibustion container assembly includes:
a container for carrying the gas-producing combustible material, the container having an opening at a bottom surface thereof;
a grip handle fixed to an external surface of the container; and
an inlet guide tube connected to the container and disposed inside the grip handle, the inlet guide tube being configured to supply air to the container.

* * * * *